US012661225B2

(12) United States Patent (10) Patent No.: US 12,661,225 B2

Schneider et al. (45) Date of Patent: Jun. 23, 2026

(54) DEVICES, SYSTEMS, AND METHODS FOR ADJUSTING THE POSITION OF AN IMPLANTABLE ELEMENT

(71) Applicant: Boston Scientific Scimed, Inc., Maple Grove, MN (US)

(72) Inventors: Lucas Schneider, Champlin, MN (US); Gregory Yiu Wah Lee, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 931 days.

(21) Appl. No.: 17/948,593

(22) Filed: Sep. 20, 2022

(65) Prior Publication Data

US 2023/0096751 A1     Mar. 30, 2023

Related U.S. Application Data

(60) Provisional application No. 63/248,012, filed on Sep. 24, 2021.

(51) Int. Cl.
A61F 2/24          (2006.01)
(52) U.S. Cl.
CPC .... A61F 2/2427 (2013.01); *A61F 2220/0016* (2013.01)
(58) Field of Classification Search
None
See application file for complete search history.

(56) References Cited

U.S. PATENT DOCUMENTS

| | | | |
|---|---|---|---|
| 9,180,005 B1 | 11/2015 | Lashinski et al. | |
| 10,335,275 B2 | 7/2019 | Lashinski et al. | |
| 10,548,731 B2 | 2/2020 | Lashinski et al. | |
| 10,555,813 B2 | 2/2020 | Lashinski et al. | |
| 2018/0228610 A1* | 8/2018 | Lashinski | A61F 2/2466 |
| 2021/0068955 A1 | 3/2021 | Bruner | |
| 2022/0096235 A1 | 3/2022 | Giese et al. | |
| 2022/0192830 A1 | 6/2022 | Schneider et al. | |

FOREIGN PATENT DOCUMENTS

WO          2021026184 A1     2/2021

OTHER PUBLICATIONS

International Search Report and Written Opinion for International Application No. PCT/US2022/044093, date of mailing Dec. 21, 2022, 13 pages.

* cited by examiner

*Primary Examiner* — Shaun L David

(74) *Attorney, Agent, or Firm* — Seager, Tufte & Wickhem, LLP

(57)          ABSTRACT

A deployment device engageable with a movable component of a medical device to actuate the movable component with respect to another component of the medical device. The deployment device may be shifted among two or more configurations or stages to permit different movements of the movable component of the medical device. For instance, in one configuration the deployment device is fully engaged with the movable component such that a portion of the movable component is inhibited from engaging with another portion of the medical device. In another configuration, the deployment device is partially withdrawn from engagement with the movable component to allow the movable component to engage with the other portion of the medical device.

12 Claims, 8 Drawing Sheets

DEVICES, SYSTEMS, AND METHODS FOR ADJUSTING THE POSITION OF AN IMPLANTABLE ELEMENT

CROSS-REFERENCE TO RELATED APPLICATIONS

This application claims the benefit of priority of U.S. Provisional Application No. 63/248,012, filed Sep. 24, 2021, the entire disclosure of which is hereby incorporated by reference herein for all purposes.

FIELD

The present disclosure relates generally to the field of implantable medical devices. In particular, the present disclosure relates to medical devices, systems, and methods for implanting an implantable medical device. More particularly, the present disclosure relates generally to improvements to medical devices, systems, and methods for adjusting the position of an implantable element, such as a movable component of an implantable device (e.g., tissue anchor), such as with respect to a portion of the implantable device (e.g., a frame member of the implantable device or an anchor housing mounted on the implantable device).

BACKGROUND

Various implantable medical device are secured to tissue using a tissue anchor. It is generally desirable to lock a movable tissue anchor with respect to the implantable device once the implantable device has been secured to tissue as desired or medically indicated, such as to prevent backout or other undesirable movement of the movable anchor. Various anchors and associated locking mechanisms involve a passive deployment process without feedback to the user, or the ability for the user to confirm positive engagement. Additionally, when an implantable device is deployed translumi-nally within the body, a deployment system with one or more flexible elongated elements may be used to deploy (including implant, and optionally also to deliver) the implantable device. The flexible elongated elements may extend at a significant enough distance through generally tortuous pathways to impact the deployment and detachment process. For instance, the process of detaching an anchor from a deployment system is generally highly dependent on the pushability of a flexible elongate member such as a 0.014" (0.356 mm) Nitinol wire through tortuous anatomical pathways. Relative movement of components of the deployment system may be needed to achieve the desired locking of the anchor in a desired deployed configuration. For instance, a locking component on the anchor may serve a dual purpose as an engagement member for engaging an actuator component of the deployment system. If such anchor locking component remains engaged by the actuator component, the anchor locking component cannot readily mate with a corresponding anchor locking feature (e.g., associated with the implantable device, such as a mating feature on an anchor housing or a part of the implantable device) to be locked in the desired anchored configuration. Locking of the anchor against further movement once the desired anchored position has been reached is thus left to chance depending on the rotational position of the anchor relative to the housing after release from the actuator component of the deployment system.

An active locking process and/or an assisted detachment process to improve the usability of a deployment system for an implantable device would be welcome in the art.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a deployment system for deploying an implantable device at a treatment device is provided. In some aspects, the implantable device has a movable component shiftable between a position in which the movable component is movable with respect to another component of the implantable device and a locked position in which a locking component associated with the movable component locks the movable component with respect to the other component of the implantable device. In some aspects, the deployment system includes a deployment device engageable with the movable component to move the movable component. In some aspects, the deployment device is shiftable between a first stage in which the deployment device is fully engaged with the movable component and the locking component thereof; a second stage in which the deployment device is operatively engaged with a portion of the movable component to move the movable component and exposes at least a portion of the locking component to allow the locking component to be moved into engagement with respect to the implantable device; and a third stage in which the deployment device is disengaged from the movable component to be withdrawn from the treatment site.

In some embodiments, the deployment device includes a tubular flexible elongate member having a distal end configured to operably engage a portion of the movable component to impart movement thereto; and a flexible elongate member extending through the flexible elongate member and having, on a distal end thereof, an actuator engagement component configured to engage a corresponding implantable device engagement component on the movable component. In some embodiments, the tubular flexible elongate member is configured to operably engage the actuator engagement component to impart movement thereto. In some embodiments, a spring assist is provided between the distal end of the tubular flexible elongate member and the distal end of the flexible elongate member to assist in movement of the distal end of the tubular flexible elongate member and the distal end of the flexible elongate member apart from each other. In some embodiments, a control device is operably coupled with the deployment device and shiftable between a first stage, a second stage, and a third stage corresponding to the first stage, second stage, and third stage of the deployment device. In some embodiments, an actuator control knob is operably coupled with the tubular flexible elongate member, and a latch control knob operably is coupled with the flexible elongate member. In some embodiments, the actuator control knob and the latch control knob are shiftable with respect to each other between first, second, and third configurations corresponding, respectively, to the first stage, the second stage, and the third stage of the control device. In some embodiments, an actuator control knob is operably coupled with the tubular flexible elongate member, and a latch control knob is operably coupled with the flexible elongate member. In some embodiments, the actuator control knob and the latch control knob are shiftable with respect to each other between first, second, and third configurations corresponding, respectively, to the first stage, the second stage, and the third stage of the control device. In some embodiments, in the first configuration, the actuator control knob and the latch control knob are a first distance apart; in the second configuration, the actuator control knob and the latch control knob are a second distance apart, the second distance being smaller than the first distance; and in the third configuration, the actuator control knob and the latch control knob are a third distance apart, the third distance being smaller than the second distance. In some embodiments, actuator control knob and the latch control knob are shaped and configured to engage each other in one of three different positions each corresponding to one of the first, second, and third configurations. In some embodiments, a movable clip is positioned between the actuator control knob and the latch control knob and movable between one of three different positions to move the actuator control knob and the latch control knob to a respective corresponding one of the first, second, and third configurations. In some embodiments, the movable clip has a varying longitudinal extent between the actuator control knob and the latch control knob and is rotatable to vary the distance between the actuator control knob and the latch control knob.

In accordance with various principles of the present disclosure, an implantable device and deployment system for the implantable device are provided. In some aspects, the implantable device has a movable component shiftable between a position in which the movable component is movable with respect to an other component of the implantable device and a locked position in which a locking component associated with the movable component locks the movable component with respect to the other component of the implantable device. In some aspects, deployment system comprises a deployment device engageable with the movable component to move the movable component. In some aspects, the deployment device is shiftable between a first stage in which the deployment device is fully engaged with the movable component and the locking component, a second stage in which the deployment device is operatively engaged with a portion of the movable component to move the movable component and exposes at least a portion of the locking component to allow the locking component to be moved into engagement with respect to the implantable device, and a third stage in which the deployment device is disengaged from the movable component to be withdrawn from engagement with the implantable device.

In some embodiments, the deployment device includes a tubular flexible elongate member having a distal end configured to operably engage a portion of the movable component to impart movement thereto; and a flexible elongate member extending through the flexible elongate member and having, on a distal end thereof, an actuator engagement component configured to engage a corresponding implantable device engagement component on the movable component. In some embodiments, the movable component of the implantable device includes an anchor having an anchor head at a proximal end thereof; the locking component is formed on the anchor head, and the implantable device engagement component is formed on the anchor head proximal to the locking component. In some embodiments, the implantable device comprises an anchor housing; the other component of the implantable device is the anchor housing; and a locking feature is formed in the anchor housing configured for locking engagement of the locking component on the anchor head therewith. In some embodiments, the distal end of the tubular flexible elongate member is configured to engage the locking component and the implantable device engagement component when the deployment device is in the first stage; in the second stage of the deployment device the distal end of the tubular flexible elongate member extends over the implantable device engagement component and the actuator engagement component in operable engagement with each other, and exposes at least a portion of the locking component to permit engagement of the locking component with the locking feature; and in the third stage of said deployment device the tubular flexible elongate member is withdrawn from the implantable device engagement component and the actuator engagement component to allow disengagement of the implantable device engagement component and the actuator engagement component from each other. In some embodiments, a spring assist is provided between the distal end of the tubular flexible elongate member and the distal end of the flexible elongate member to assist in distal movement of the distal end of the flexible elongate member with respect to the distal end of the tubular flexible elongate member to rotate and engage the locking component with the locking feature.

In accordance with various principles of the present disclosure, a method of deploying an implantable device includes delivering an implantable device operably engaged with a distal end of a deployment device to a treatment site, with the deployment device in a first stage in which the deployment device is fully engaged with a movable component of an implantable device and a locking component on the movable component; actuating the deployment device, when in the first stage, to implant the movable component; shifting the deployment device to a second stage in which the deployment device exposes at least a portion of a locking component on the movable component of the implantable device yet remains operably engaged with an actuator engagement component and an implantable device engagement component operably engaged with each other; actuating the deployment device, when in the second stage, to actuate the actuator engagement component to move a locking component of the movable component of the implantable device into operable engagement with a locking feature on an other component of the implantable device to inhibit further movement of the movable component; and shifting the deployment device to a third stage in which the deployment device is withdrawn from operable engagement with the actuator engagement component and the implantable device engagement component to allow the actuator engagement component and the implantable device engagement component to disengage from each other to allow the deployment device to be withdrawn from the implantable device.

In some embodiments, the method includes shifting a control device operably engaged with the deployment device between a first stage, a second stage, and a third stage to shift the deployment device respectively between the first stage, second stage, and third stage of the deployment device.

In some embodiments, the implantable device comprises an anchor and an anchor housing, and the method further comprises advancing the anchor relative to the anchor housing and into tissue when the deployment device is in the first stage; and locking the anchor relative to the anchor housing when the deployment device is in the second stage.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
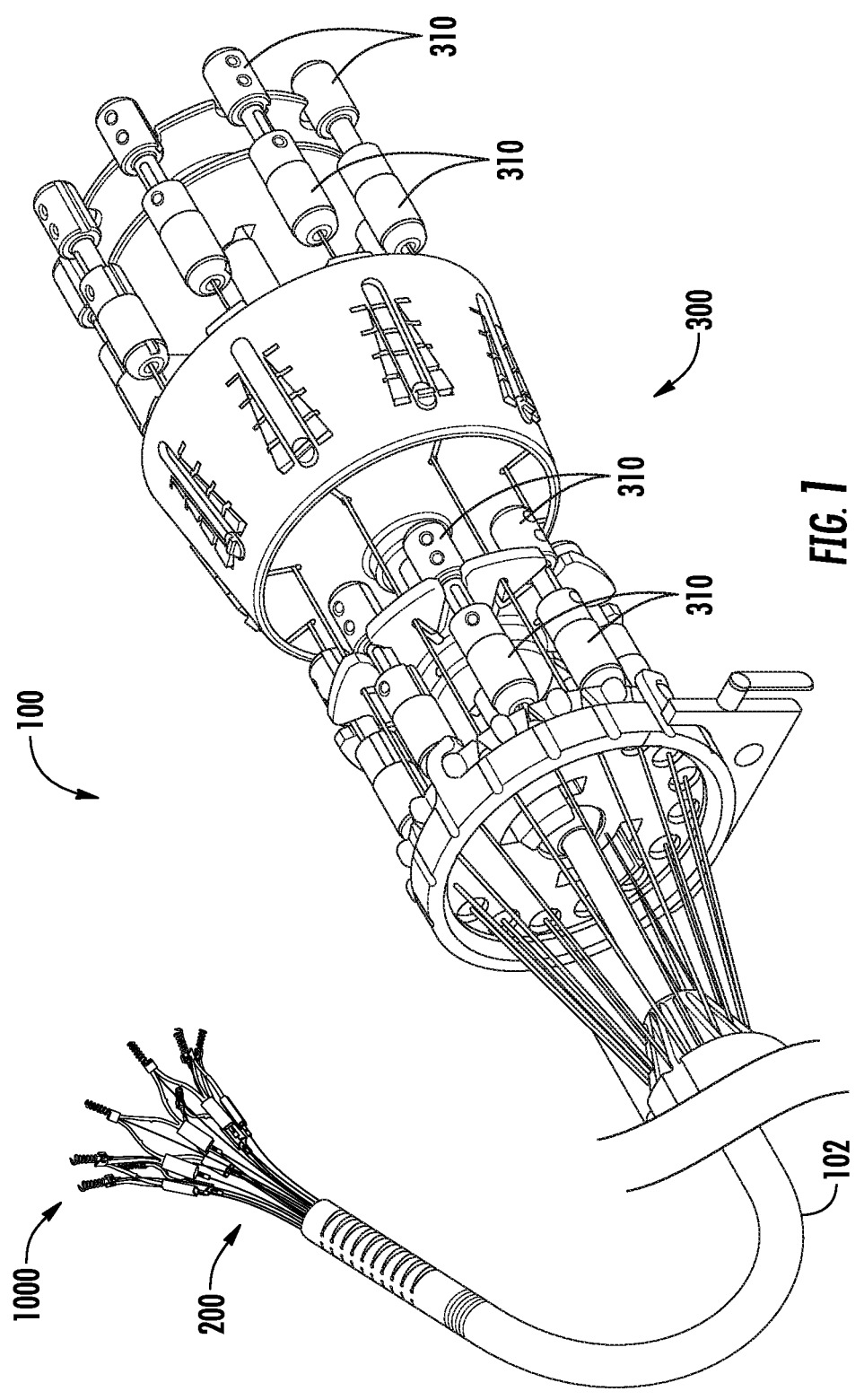
FIG. 1 illustrates a perspective view of an example of a delivery/deployment system formed in accordance with aspects of the present disclosure, showing an example of a control handle assembly at a proximal end thereof and an example of an implantable device at a distal end thereof, with intermediate sections therebetween, between break lines, not shown for the sake of simplicity.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a strut, a channel, a cavity, or a bore. As used herein, "bore" is not limited to a circular cross-section. As used herein, a "free end" of an element is a terminal end at which such element does not extend beyond In accordance with an aspect of the present disclosure, an implantable device is actuatable in more than one manner. In accordance with another aspect of the present disclosure, an implantable device is deployed at a treatment site (e.g., anchored to tissue at the treatment site) with a deployment system configured to engage an implantable device in more than one mode of engagement. For instance, the deployment system may be configure not only to deploy the implantable device, but also to facilitate locking of a movable component of the implantable device against movement, such as against movement with respect to one or more other components of the implantable device. In accordance with various principles of the present disclosure, a deployment system includes a deployment device configured to be operably (alternatively referenced herein as operatively without intent to limit) engaged with a movable component of an implantable device in one or more stages. It will be appreciated that the term stage may be used interchangeably herein with terms such as configuration, position, etc., without intent to limit. As used herein, reference to operably (or operatively) engaged generally describes when the deployment device is engaged with the implantable device to impart movement thereto. Such movement may include rotational and/or translatory (generally linear, such as axial) movement during, but not limited to, delivery and deployment of the implantable device. It will be appreciated that terms such as engaged, coupled, connected, etc. (and other grammatical forms thereof) may be used interchangeably herein without intent to limit unless otherwise specified. The deployment device generally may be configured to facilitate transference of movement of the deployment device to the movable component of the implantable device. For instance, a component of the deployment device may be configured to engage with at least the movable component of the implantable device to impart movement of the deployment device to the movable component of the implantable device. It will be appreciated that terms such as transfer, impart, transmit, convey, and the like (and other grammatical forms thereof) may be used interchangeably herein without intent to limit unless otherwise specified. Examples of a steerable delivery/deployment device and system with various positioning and imaging capabilities to which various principles of the present disclosure may be applied as described in U.S. Pat. No. 10,335,275, titled Methods For Deployment Of Heart Valve Devices Using Intravascular Ultrasound Imaging, and issued on Jul. 2, 2019; and in U.S. Pat. No. 10,555,813, titled Implantable Device And Delivery System For Reshaping A Heart Valve Annulus, and issued on Feb. 11, 2020, which patents are incorporated herein by reference in their entirety for all purposes.

In accordance with various principles of the present disclosure, the deployment device is shiftable between at least three stages. It will be appreciated that terms such as shift (including other grammatical forms thereof) may be used interchangeably herein with such terms (and other grammatical forms thereof) as move, transition, advance, etc., without intent to limit. In at least one of the stages of the deployment device, the deployment device operably engages the movable component of the implantable device to actuate the movable component of the implantable device. It will be appreciated that terms such as actuate (including other grammatical forms thereof) may be used interchangeably herein with such terms (and other grammatical forms thereof) as move, control, maneuver, manipulate, operate, drive, advance, retract, rotate, translate, etc., without intent to limit.

In the first stage, the deployment device is operably engaged with the movable component of the implantable device to move the movable component of the implantable device as desired with respect to other components of the implantable device. For instance, in an embodiment in which the movable component of the implantable device is an anchor, the deployment device is operably engaged with the anchor to implant the anchor into tissue to secure the implantable device to the tissue. It will be appreciated that terms such as secure, affix, implant, couple, engage, anchor, hold, retain, etc., and other grammatical forms thereof, may be used interchangeably herein without intent to limit. It will further be appreciated that principles of the present disclosure are not necessarily limited to such embodiment. For instance, principles of the present disclosure may be applied to other engagements and/or movements of a deployment device with respect to a medical device, such as, without limitation, to actuate a component of an implantable device to facilitate implantation thereof, or to manipulate a device at a treatment site, such as to adjust the position, configuration, etc., of the device.

In accordance with various principles of the present disclosure, the movable component of the implantable device includes a locking component configured to engage with a mating locking feature associated with the implantable device. The locking component is configured to mate with the locking feature for secure engagement therewith. The locking feature may be provided or formed on a component of the implantable device with respect to which the movable component selectively moves (before engagement of the locking component with the locking feature). The locking component and locking feature are selectively engageable with each other in a locking configuration to lock the movable component of the implantable device from movement with respect to at least the component on which the locking feature is formed, and optionally also with respect to other components of the implantable device. In the first stage of the deployment device, the deployment device operably engages the locking component of the movable component. In some embodiments, the deployment device is operably engaged with the locking component to facilitate actuation of the movable component of the implantable device by the deployment device. For instance, in some embodiments, the deployment device is configured to mate with the locking component to facilitate transference of movement of the deployment device to the movable component of the implantable device, such as via the locking component. In some embodiments, the deployment device includes an actuator or driver configured to operably engage the movable component of the implantable device to impart movement thereto. It will be appreciated that engagement of the deployment device with the locking component generally inhibits full operable engagement of the locking component with the locking feature so that the deployment device can impart movement to the locking component without interference of the locking feature.

In some embodiments, the deployment device includes an actuator engagement component configured to engage with a corresponding implantable device engagement component on the movable component with which the deployment device is operably engaged. The engagement components are configured to mate with each other for secure engagement with each other to prevent inadvertent decoupling (separation) thereof and to operably engage the deployment device and the implantable device to permit movement of the deployment device to be imparted to the movable component of the implantable device. For instance, the engagement component on the deployment device may be configured to matingly engage with a corresponding engagement component on the implantable device, such as to interlock or otherwise to fit together in secure contact. Such engagement components may be latches, couplers, connectors, etc. or other equivalent structures known to those of ordinary skill in the art, reference begin made herein to a latch for the sake of convenience and without intent to limit.

In the second stage, the deployment device is shifted with respect to the movable component of the implantable device to facilitate engagement of the locking component with the locking feature associated with the implantable device. For instance, in some embodiments, when the deployment device is in the first stage, the locking component is engaged by the deployment device and not positioned or otherwise arranged to be able to engage fully with the locking feature associated with the implantable device. Shifting of the deployment device to the second stage allows the locking component to be engaged fully with the locking feature. For instance, in some embodiments, in the first stage, the deployment device blocks at least a portion of the locking component to prevent such portion of the locking component from engaging with the locking feature. In such embodiment, when the deployment device is moved to the second stage, the deployment device is shifted into a position with respect to the locking component to permit the locking component to operably engage with the locking feature a sufficient extent to lock with respect to the component in which the locking feature is formed. For instance, in the first stage, a component of the deployment device covers the locking component, whereas in the second stage component of the deployment device uncovers the locking component. It will be appreciated that terms (and other grammatical forms thereof) such as cover, enclose, sheathe, etc. may be used interchangeably herein without intent to limit. Likewise, terms such as uncover, expose, unsheathe, etc. (and other grammatical forms thereof) may be used interchangeably herein without intent to limit. In some embodiments, the deployment device may remain partially operably engaged with the locking component when in the second stage to impart movement thereto while exposing a sufficient extent of the locking component to be moved into engagement with the locking feature. The modified operable engagement of the deployment device with the movable component (such as via the operably engaged latches) when the deployment device is in the second stage allows the deployment device to move the locking component of the movable component into engagement with the locking feature. It will be appreciated that once the locking component engages the locking feature, the deployment device would no longer be able to impart movement to the movable component of the implantable device, whether or not the deployment device is or is not engaged with the locking component. The deployment device may, nonetheless, be capable of imparting torque to the locking component, but the locking component generally will not move with respect to the locking feature. If the actuator engagement component of the deployment device remains engaged with the implantable device engagement component, then the locking component optionally may be reengaged with the deployment device (returning the deployment device and the movable component to a configuration at least analogous to the second stage if not actually the configuration of the second stage), so that movement of the deployment device may move the movable component again.

In embodiments in which the deployment device includes an actuator latch and the movable component of the implantable device includes a corresponding component latch engageable by the actuator latch, such latches remain operably engaged with each other when the deployment device is in the second stage. Operable engagement of such latches allows movement of the deployment device to continue to move the movable component of the implantable device while the deployment device is in the second stage. It will be appreciated that other engagements between the deployment device and at least a portion of the movable component of the implantable device may allow movement of the deployment device to continue to move the movable component of the implantable device when the deployment device is in the second stage.

In the third stage, the deployment device is released from operable engagement with the movable component of the implantable device so that the implantable device may be deployed and the deployment device withdrawn. The implantable device may then be left in its extended use position/configuration (e.g., implanted) within the body.

In some embodiments, the deployment device includes a flexible elongate member (such as in the form of a wire, shaft, tube, etc.) with an engagement component (reference being made to a latch for the sake of convenience and without intent to limit, as discussed above), at a distal end thereof (generally coupled thereto in any manner known in the art, the disclosure not being limited to a particular manner of coupling). The movable component of the implantable device includes a mating engagement component (reference being made to a latch for the sake of convenience and without intent to limit, as discussed above) configured to operably couple with the latch of the flexible elongate member to operably couple the flexible elongate member and the implantable device together. Operable coupling of the corresponding latches of the deployment device and the implantable device allows movement of the flexible elongate member to be imparted to the implantable device (to be understood herein as the entire implantable device or simply a component thereof). The flexible elongate member is configured to extend to the implantable device from a control assembly (outside the body of the patient) through a tortuous pathway within the body to the treatment site, and to transmit torques imparted to the proximal end of the flexible elongate member (by a control assembly) to the implantable device coupled to the distal end of the flexible elongate member.

In some embodiments, the deployment device further includes a tubular flexible elongate member extending over the flexible elongate member with the actuator latch. Such tubular flexible elongate member may be in the form of a hollow shaft or tube or hypotube, etc., and may be alternately referenced herein, without intent to limit, as an actuator, driver, driver shaft, driver tube, etc. The tubular flexible elongate member is configured to selectively operably engage the latches of the flexible elongate member and the implantable device to impart movement to the movable component of the implantable device (e.g., such as to manipulate the movable component of the implantable device). The tubular flexible elongate member may also be configured to selectively operably engage the locking component of the implantable device to impart movement to the movable component of the implantable device (e.g., such as to manipulate the movable component of the implantable device) via the locking component. For instance, the tubular flexible elongate member may be configured (e.g., with mating non-circular engagement surfaces) to nonrotatably engage with the actuator latch and/or the implantable device component latch to actuate rotation of the implantable device/movable component. Additionally or alternatively, the tubular flexible elongate member may be configured (e.g., with mating non-circular engagement surfaces) to nonrotatably engage with a portion of the component of the implantable device to be actuated (such as the locking component).

In accordance with various principles of the present disclosure, in embodiments of deployment devices including a flexible elongate member extending through a tubular flexible elongate member, the tubular flexible elongate member extends over the flexible elongate member to engage the locking component of the movable component of the implantable device when the deployment device is in the first stage. In such embodiment, when the deployment device is in the second stage, the tubular flexible elongate member is proximally withdrawn with respect to the flexible elongate member to allow the locking component to engage with a locking feature. For instance, the tubular flexible elongate member may be proximally withdrawn to expose a sufficient portion or extent of the locking component to be able to operably engage with and lock with the locking feature. Additionally or alternatively, tension on the flexible elongate member may be released to allow the flexible elongate member to be advanced distally with respect to the tubular flexible elongate member to advance the locking component into engagement with the locking feature. In the third stage of such embodiment of a deployment device, the tubular flexible elongate member no longer holds the flexible elongate member in engagement with the implantable device so that both the tubular flexible elongate member and the flexible elongate member may be withdrawn from the implantable device.

In some embodiments, a spring assist is provided between the tubular flexible elongate member and the flexible elongate member to assist relative movement therebetween when the deployment device is shifted into the second stage. More particularly, in some embodiments, when the deployment device is shifted into the second configuration, tension may be released from the flexible elongate member to allow distal advancement of the flexible elongate member and/or retraction of the tubular flexible elongate member (proximally relative to the flexible elongate member) to unsheathe at least a portion of the locking component on the implantable device. To assist in such relative movement such that the distal end of the flexible elongate member will extend from (be outside and distal to) the distal end of the tubular flexible elongate member to be able to distally advance the distal end of the flexible elongate member to advance the locking component into engagement with the locking feature, a biasing element (such as a spring) may be arranged with respect to the distal end of the flexible elongate member and the distal end of the tubular flexible elongate member. The biasing element may be in a loaded state storing potential energy (such as a compressed coil spring) when the deployment device is in the first stage. The potential energy stored in the biasing element is released upon shifting of the deployment device to the second configuration to assure that the distal end of the flexible elongate member is not retracted with the distal end of the tubular flexible elongate member and/or to assure the distal end of the tubular flexible elongate member retracts proximally with respect to the distal end of the flexible elongate member to expose the locking component (which is coupled with the distal end of the flexible elongate member), and/or to facilitate distal advancement of the distal end of the flexible elongate member to advance the locking component into engagement with the locking feature.

The tubular flexible elongate member and the flexible elongate member may extend proximally to a proximal end controlled by a control handle. The control handle may include an actuator control knob operably coupled with the tubular flexible elongate member, and a latch control knob operably coupled with flexible elongate member. The actuator control knob and the latch control knob are movable with respect to each other to shift the deployment device between the first, second, and third stages described above. Various configurations of control handles may be formed in accordance with various principles of the present disclosure to allow such relative movement. In some embodiments, the knobs may be locked with respect to each other in each of the positions or stages corresponding to the stages of the deployment device to inhibit or prevent inadvertent relative movement which could result in shifting of the deployment device into a different stage.

Although the principles of the present disclosure are described with reference to deployment and/or implantation of an implantable device, it will be appreciated that various principles of the present disclosure are applicable to delivery, adjustment, and/or other manipulations of an implantable device or other medical devices. For instance, principles of the present disclosure, may be applied to various devices, including but limited to actuator devices, capable of being navigated through a tortuous path within the human body and configured to engage a portion of a device such as an implantable device to manipulate (e.g., deploy, configure, reconfigure, position, reposition, implant, etc.) the implantable device. It will be appreciated that the devices may be considered to be part of an associated system, such as part of a delivery and deployment system used to deliver and deploy an implantable device to a treatment site. However, for the sake of convenience, and without intent to limit, reference herein is limited to the deployment aspect of the system as improvements disclosed herein are generally associated with release of the system from the device after deployment of the device. The deployment device thus may be configured to remain coupled with the implantable device during delivery to a treatment site and during deployment of the implantable device at the treatment site, such as during manipulation of the implantable device to be deployed in a desired configuration, at a desired location, etc., and/or to be secured to the treatment site as desired or medically indicated. Reference may be made herein to delivery and/or deployment and/or implantation and/or adjustment of the implantable device interchangeably with one another or other similar terms without intent to limit.

In some embodiments, the delivery/deployment system is used to implant an implantable device having one or more anchors that may be advanced into tissue at a treatment site. The anchor may be movably coupled to the implantable device such that movement (e.g., rotation or translation) of the anchor with respect to the implantable device causes the anchor to advance into tissue at the treatment site to secure the implantable device thereto. In some embodiments, one or more anchor housings may be provided, each housing or carrying an anchor. An anchor may be coupled to the implantable device via an anchor housing, with the anchor housing being generally fixed with respect to the implantable device such that anchor moves with respect to the anchor housing and with respect to the implantable device. In order to secure the implantable device to tissue and to minimize or prevent undesired movement of the anchor relative to the treatment site (and consequent movement of the implantable device relative to the treatment site which may cause loosening, dislodgment, separation, etc., of the implantable device), it is desirable to provide the anchor and the implantable device (and/or the anchor housing, if provided) with a locking component and corresponding locking feature. For instance, the anchor may include one or more locking components shaped and configured to engage with a corresponding locking feature on the implantable device and/or anchor housing (if provided) to prevent further movement of the anchor (e.g., backout, retraction, detachment, etc.) after the anchor has been advanced the desired extent into tissue to secure the implantable device thereto. It will be appreciated that until such desired final position has been reached, it may be desirable to retract the anchor as needed (such as to reposition the anchor, adjust the anchor depth, etc.). The movable components in the examples of embodiments illustrated in the accompanying figures are anchors. However, other movable components are within the scope and spirit of the present disclosure, the principles of the present disclosure not being limited to anchors.

It will be appreciated that various principles of the present disclosure may be applied to other components of a deployment device for which staged relative movement or actuation may be desired, the present disclosure not being limited to anchor actuators and anchors with locking components.

Various embodiments of deployment devices formed in accordance with various principles of the present disclosure will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein.

Turning now to the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, certain features in one embodiment may be used across different embodiments and are not necessarily individually labeled when appearing in different embodiments.

An example of a deployment system 100 for deployment of (and/or other action associated with) an implantable device 1000 to a treatment site is shown, in a perspective view, in FIG. 1. In the illustrated example of an embodiment, the implantable device 1000 is carried by or coupled to or otherwise associated with the deployment system 100 and may be considered in some instances to be part of the deployment system 100. The deployment system 100 may include a steerable delivery device 102 (e.g., catheter, sheath, or the like) through which the implantable device 1000 may be delivered (e.g., transluminally) to a treatment site. The illustrated example of an embodiment of an implantable device 1000 is shiftable between a contracted deployment configuration (not illustrated, but in which the implantable device 1000 may be delivered through the steerable delivery device 102 to the treatment site) and an expanded configuration as illustrated in FIG. 1. The deployment system 100 includes one or more deployment devices 200 formed in accordance with various principles of the present disclosure to facilitate deployment of the implantable device 1000 and securing of the implantable device 1000 to a treatment site. The steerable delivery device 102 may be controlled (e.g., steered or navigated) by a control device 300 formed in accordance with various principles of the present disclosure and including one or more delivery device control knobs 310 (for example, a control knob 310 associated with each deployment device 200). It will be appreciated that the control device 300 may include more than one set of control knobs, each set controlling or actuating a different component of the deployment device 200.

Turning to FIGS. 2A, 2B, 3, and 4, an example of an embodiment of a deployment device 200 formed in accordance with various principles of the present disclosure is illustrated in further detail. The illustrated deployment device 200 may be used with the deployment system 100 illustrated in FIG. 1. A distal end 201 of the deployment device 200 is illustrated operably coupled with a movable component 1010 of an example of an embodiment of an implantable device 1000. In the illustrated example, the embodiment of a movable component 1010 of an implantable device 1000 is a component of an anchor assembly 1020 shown isolated from the implantable device 1000 for the sake of clarity and simplicity. However, principles of the present disclosure need not be limited to anchor systems. It will be appreciated that, for the sake of clarity, the proportions/scale of element of the deployment device 200 have been adjusted (increased) relative to proportions of the movable component 1010 and its associated elements. A proximal end 203 of the deployment device 200 is illustrated operably coupled with a control device 300 formed in accordance with various principles of the present disclosure and which may be used with the deployment system 100 of FIG. 1. In some aspects, the deployment device 200 and/or the control device 300 may be considered a part of the deployment system 100 illustrated in FIG. 1. Additional components and/or devices associated with the deployment device 200, control device 300, and/or the deployment system 100 are not illustrated in order to simplify the illustration for the sake of clarity with respect to the depiction and description of the illustrated example of an embodiment of a deployment device 200 and a control device 300.

The deployment device 200 may be in the form of an actuator with various features known in the art, and may (or components thereof may) be alternately referenced herein as an actuator or driver or controller (with or without the term "mechanism") without intent to limit. It will be appreciated that the term actuate (including other grammatical forms thereof) may be used interchangeably herein with such terms (and other grammatical forms thereof) as control, maneuver, manipulate, move, operate, drive, shift, transition, advance, retract, rotate, translate, etc., without intent to limit. In the illustrated example of an embodiment, the deployment device 200 includes a flexible elongate member 210 (e.g., extending through a lumen defined in a tubular flexible elongate member 220, shown in phantom and described in further detail below) with an actuator latch 212 at a distal end 211 of the flexible elongate member 210. The actuator latch 212 is configured to engage a component latch 1012 on a proximal end 1013 of the movable component 1010.

The deployment device 200 may further include a tubular flexible elongate member 220 (e.g., a hollow shaft or tube or hypotube) extending over flexible elongate member 210. The example of an embodiment of a tubular flexible elongate member 220 illustrated in FIGS. 2A, 2B, 3, and 4 includes a latch cover 222 on a distal end 221 thereof configured to extend over the actuator latch 212 and the component latch 1012 to hold the actuator latch 212 with respect to the component latch 1012, such as may be appreciated with reference to the cross-sectional view of FIG. 2B along line II-II of FIG. 2A. It will be appreciated that the interior contour of at least the latch cover 222 (and optionally additional portions of the tubular flexible elongate member 220) may be configured to mate with the exterior contours of the actuator latch 212 and the component latch 1012 to allow movement of the tubular flexible elongate member 220 to be transmitted to the actuator latch 212 and the component latch 1012 via the latch cover 222. For instance, such components may have non-rounded or otherwise contoured mating surfaces to impart rotational movement therebetween to transmit torque from the tubular flexible elongate member 220 to the movable component 1010. For instance, in an embodiment in which the movable component 1010 is an anchor system, movement of the tubular flexible elongate member 210 may actuate the anchor system to advance or retract an anchor component thereof, such as into tissue at a site at which the implantable device 1000 is to be anchored. In such embodiment, the latch cover 222 may be considered an anchor cover.

The latch cover 222 may be retracted to allow disengagement/decoupling of the actuator latch 212 and the component latch 1012 once the desired position of the movable component 1010 has been attained and/or the implantable device 1000 is implanted as desired/medically indicated, as described in further detail below.

In accordance with various principles of the present disclosure, the tubular flexible elongate member 220 is configured to engage a locking component of the movable component 1010 of the implantable device 1000. In some embodiments, the latch cover 222 of the tubular flexible elongate member 220 is configured to engage a locking component of the movable component 1010 of the implantable device 1000. In some embodiments, in at least one position, the tubular flexible elongate member 220 is operably engaged with a locking component of the movable component 1010 of the implantable device 1000 to permit movement (e.g., rotational movement) of the tubular flexible elongate member 220 to be imparted to the locking component to actuate the movable component 1010, as will be further described below.

In the example of embodiments illustrated in FIGS. 2A, 2B, 3, and 4, the movable component 1010 of the implantable device 1000 may be a component of an anchor assembly 1020 coupled to the implantable device 1000 to secure the implantable device 1000 to a treatment site (e.g., to tissue at the treatment site). The implantable device 1000 may be anchored with respect to an implant site/treatment site with one or more anchor assemblies 1020. In the illustrated embodiment, the anchor assembly 1020 includes at least one anchor 1030, configured to secure the implantable device 1000 to the treatment site TS. In some embodiments, the anchor 1030 are movable with respect to the implantable device 1000 and are considered the movable component of the implantable device referenced herein. The anchor 1030 may extend distally from the implantable device 1000 and may have a sharpened distal tip to penetrate and to facilitate entry and advancement into tissue at a treatment site. The anchors 4030 may include an anchor shaft 1032 and an anchor head 1034. The anchor shaft 1032 may be in the form of helical coil, as in the example of an embodiment illustrated in FIGS. 2A, 2B, 3, and 4, or an elongated element with a plurality of external threads, reference being made herein to "turns" of a coil or threads for the sake of convenience and without intent to limit. In accordance with various principles of the present disclosure, the anchor head 1034 includes a locking component 1036 configured to lockingly engage a component of the implantable device 1000 to hold the anchor 1030 from moving with respect to the implantable device 1000. In the example of an embodiment illustrated in FIGS. 2A, 2B, 3, and 4, the locking component 1036 is at least one (and, optionally two, as illustrated) laterally (e.g., radially) outwardly extending tabs. In some embodiments, the anchor assembly 1020 includes an anchor housing 1040 via which the anchor 1030 is mounted or coupled to the implantable device 1000. The anchor housing 1040 may be coupled to the implantable device 1000 in any desired manner acceptable to those of ordinary skill in the art, such as in view of the structure of the implantable device 1000 (e.g., welding, brazing, adhering, mechanical engagement such as interference fit, etc., without limitation, the particular manner of retention not being critical to the principles of the present disclosure). In an embodiment of an anchor assembly 1020 including an anchor housing 1040, the locking component 1036 may engage with a locking feature 1046 formed on the anchor housing 1040. For instance, in the example of an embodiment illustrated in FIGS. 2A, 2B, 3, and 4, the locking component 1036 is a laterally (radially) extending tab fitting within a correspondingly shaped/configured locking recess in a proximal end 1043 of the anchor housing 1040. The term tab may be used interchangeably herein with flange or projection or the like without intent to limit. It will be appreciated that other locking components and features are within the scope of the present disclosure. The anchor 1030 advances or retracts through an anchor bore 1045 defined through (e.g., axially through) the anchor housing 1040. The anchor 1030 may be guided within the anchor bore 1045 of the anchor housing 1040 by mating of the turns of the anchor shaft 1032 with internal threads or grooves on the inner wall in the anchor bore 1045. The anchor bore 1045 may include an unthreaded distal section 1047 (closer to the distal end 1041 of the anchor housing 1040) in which the proximal turns of the anchor 1030 may be positioned when the anchor 1030 is substantially fully deployed to allow for "free spin" of the anchor 1030 (drawing tissue proximally towards the anchor housing 1040 without advancing the anchor 1030 distally with respect to the anchor housing 1040). More particularly, in some embodiments, the anchor 1030 may be distally advanced into the tissue until the proximal-most turn of the anchor shaft 1032 is positioned within the unthreaded distal section 1047 in the anchor bore 1045 of the anchor housing 1040. Once the turns of the anchor 1030 are no longer engaged with the threads in the anchor housing 1040, further rotation of the anchor 1030 does not result in further distal advancement of the anchor 1030, but may result in tissue being drawn proximally towards the anchor housing 1040 to improve affixation of the anchor assembly 1020 to the tissue. Undesired distal advancement of the anchor 1030 through (and beyond or out of) the anchor housing 1040 may be prevented by abutment of the locking component 1036) on the anchor head 1034 with a proximal end 1043 of the anchor housing 1040, as may be appreciated with reference to FIG. 4. Additionally, once the locking component 1036 and the locking feature 1046 are matingly engaged, the anchor 1030 is prevented from being rotated to retract out of the deployed configuration and/or unintentionally backing out of the anchor housing 1040. Any of a variety of additional features may be provided on the anchor shaft 1032 and/or within the anchor bore 1045 to prevent or inhibit unintended or undesired proximal withdrawal of the anchor 1030 from the anchor housing 1040. Various additional features of anchor assemblies may be appreciated with reference to the following patents and patent applications, each of which is incorporated herein by reference in its entirety for all purposes: U.S. Pat. No. 10,548,731 to Lashinski et al., titled Implantable Device and Delivery System for Reshaping a Heart Valve Annulus; and U.S. Patent Application Publication 2021/0068955, published on Mar. 11, 2021, and titled Spring Loaded Self Locking Reversible Anchor; and U.S. Patent Application Publication US2022/01928730 published on Jun. 23, 2022, and titled Anchoring Devices, Assemblies, And Methods For Implantable Devices.

Figure 2A:
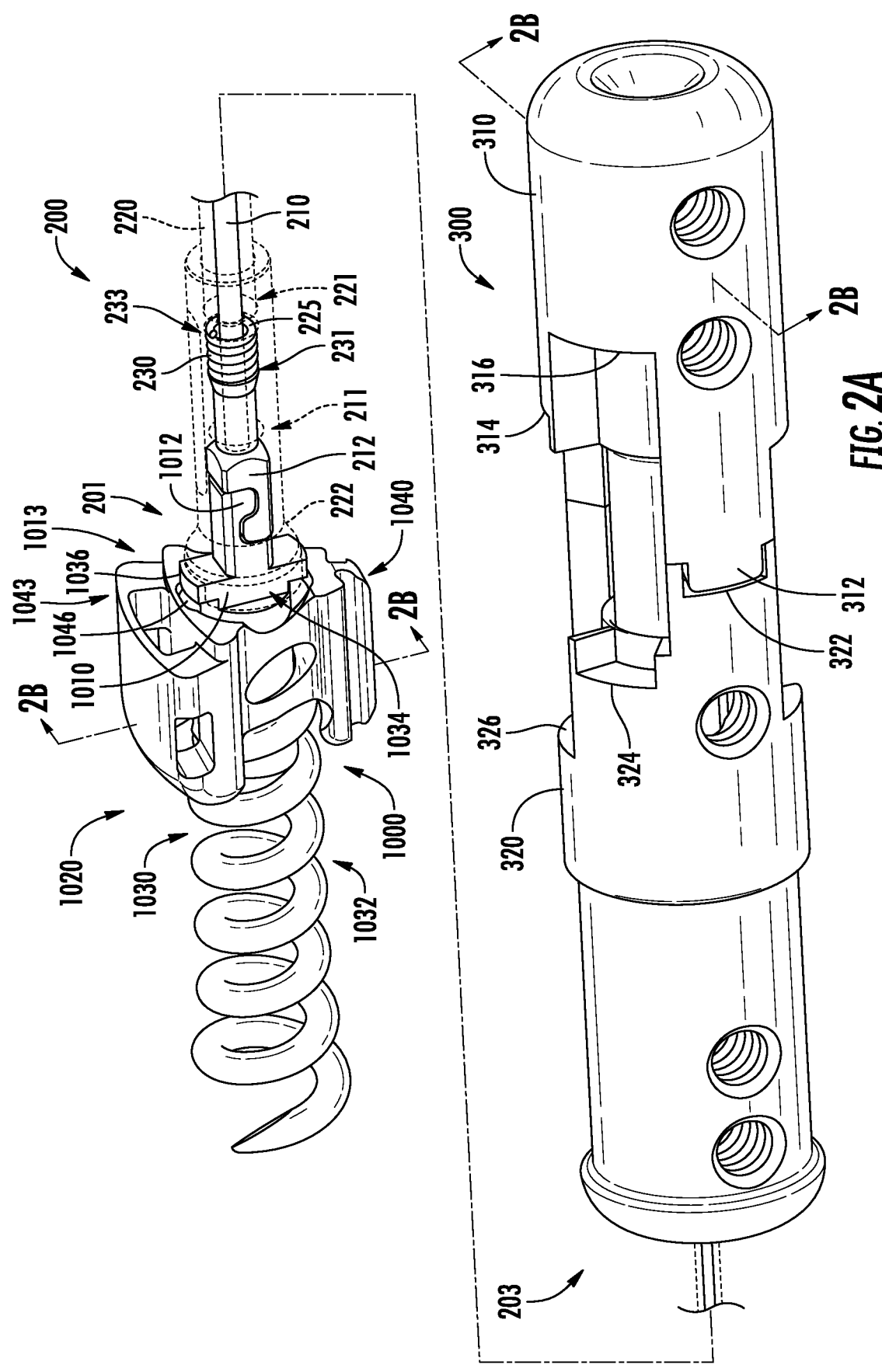
FIG. 2A illustrates a simplified perspective view of an example of an anchor actuator engaging an example of an anchor of an implantable device in accordance with various principles of the present disclosure, with other associated components and devices not shown for the sake of simplicity.
Figure 2B:
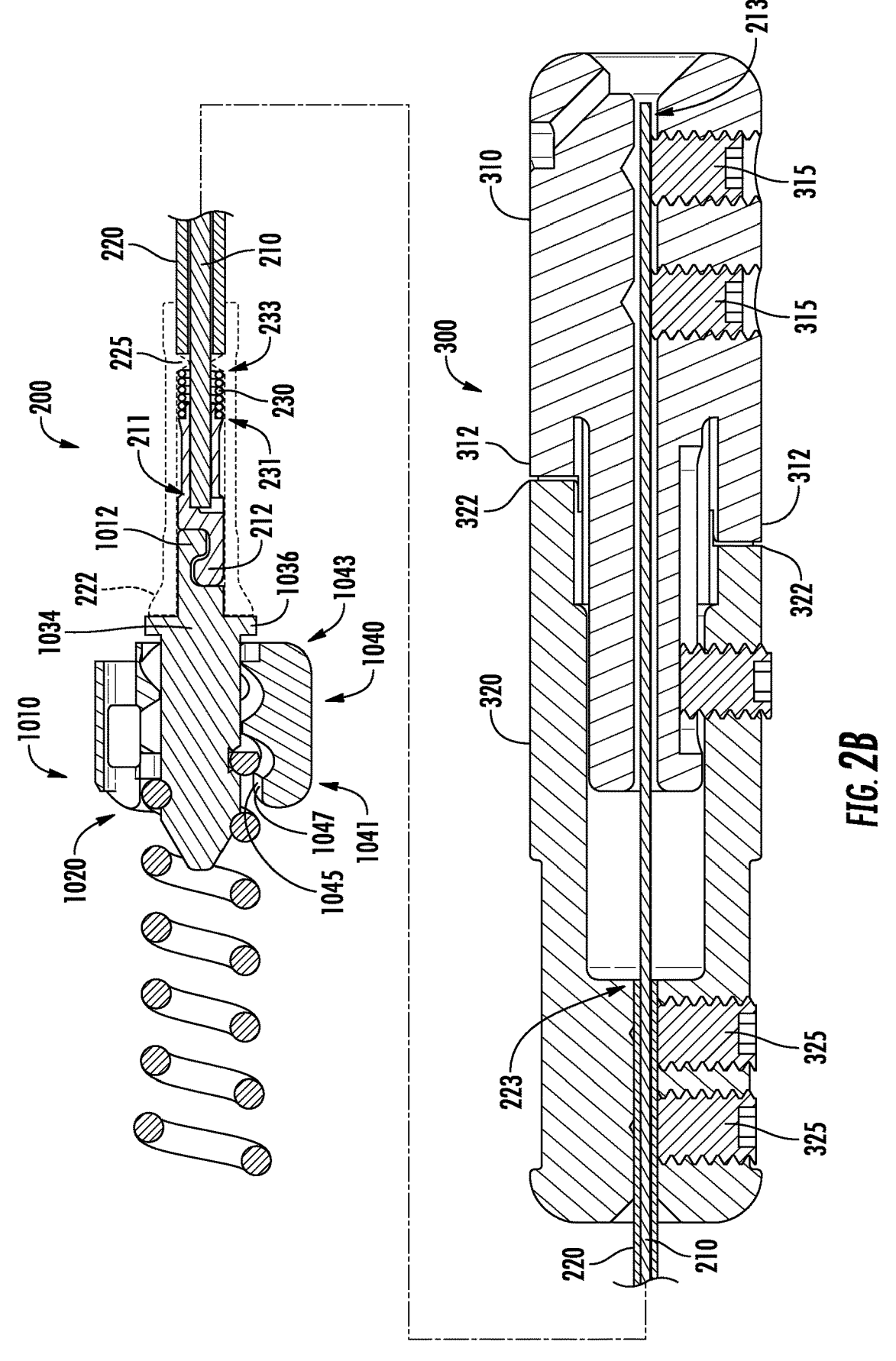
FIG. 2B illustrates a cross-sectional view along line II-II of FIG. 2A.

As may be appreciated with reference to FIG. 2A and FIG. 2B, illustrating an implantable device 1000 in the form of an anchor assembly 1020, when the latch cover 222 (which may be considered an anchor cover) is positioned over the actuator latch 212 and the component latch 1012, the latch cover 222 also is positioned over the locking component 1036 of the anchor assembly 1020 (more particularly, of the anchor 1030). Such configuration of the deployment device 200 may be referenced herein as the first stage of the deployment device 200. In the first stage, the latch cover 222 operably engages the actuator latch 212, the component latch 1012, and the locking component 1036 to impart movement (e.g., rotational movement) thereto to actuate the anchor 1030.

Figure 3:
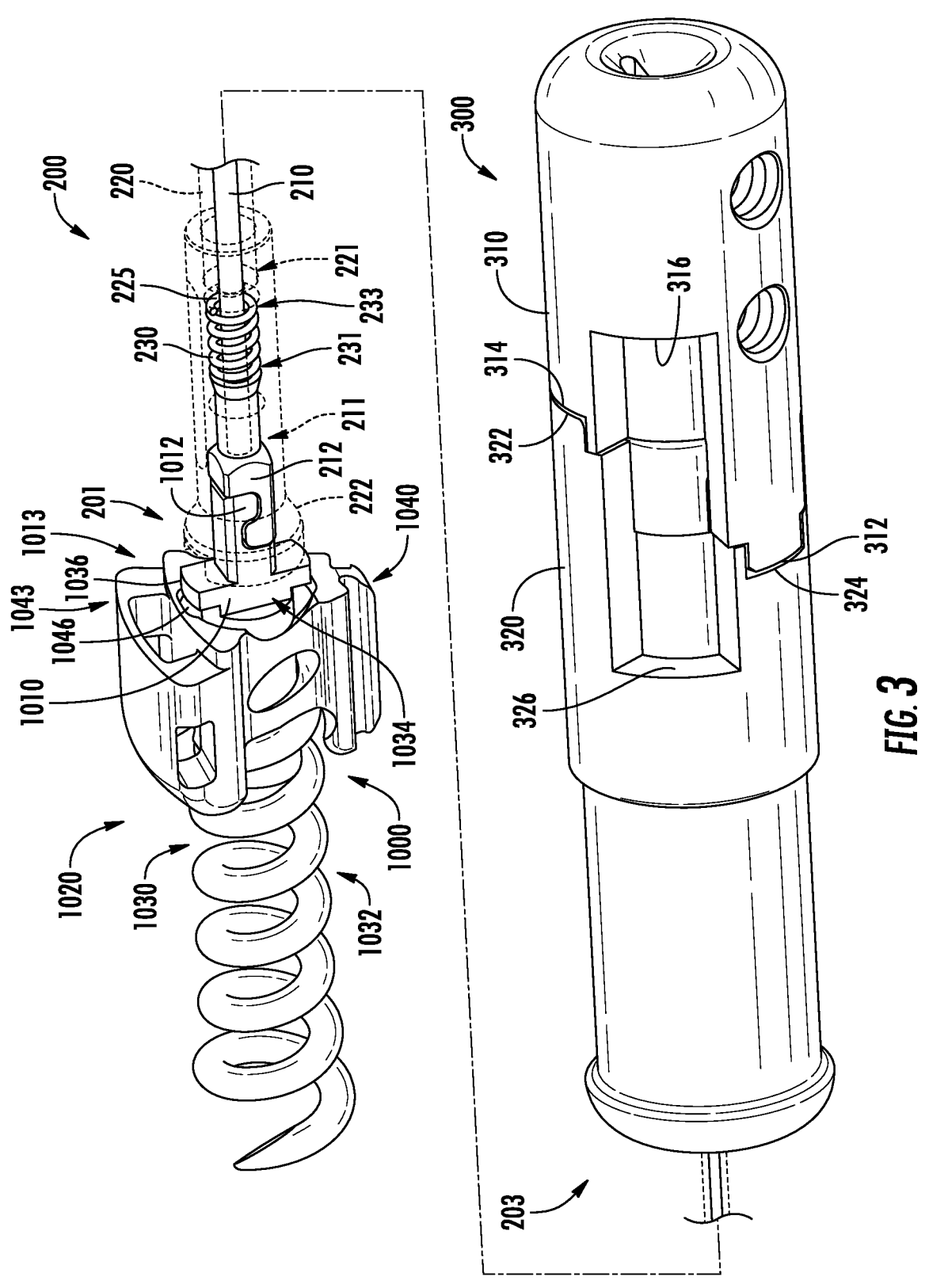
FIG. 3 illustrates a view similar to that of FIG. 2A, but with the anchor cover withdrawn to expose a portion of the anchor head.

Once the anchor 1030 has been fully advanced, and it is desired to prevent retraction of the anchor 1030, the deployment device 200 may be shifted to the second stage, illustrated in FIG. 3. More particularly, in the second stage of the deployment device 200, the tubular flexible elongate member 220 is proximally retracted with respect to the flexible elongate member 210 to proximally retract the latch cover 222 to uncover at least a portion of the locking component 1036. Because the latch cover 222 remains operably engaged with the actuator latch 212 and the component latch 1012, movement of the tubular flexible elongate member 220 may still be imparted to the movable component 1010 (in the illustrated example of an embodiment, the anchor 1030), such as via the actuator latch 212. A portion of the locking component 1036 may remain in partial operable engagement with the latch cover 222 so that movement of the tubular flexible elongate member 220 may still be imparted to the movable component 1010 (in the illustrated example of an embodiment, the anchor 1030) via the locking component 1036 as well. However, a sufficient portion of the locking component 1036 is exposed when the deployment device 200 is in the second stage to permit the tubular flexible elongate member 220 to rotate the anchor 1030 and the locking component 1036 so that the locking component 1036 operably engages with the locking feature 1046 and further rotation of the anchor 1030 is thereby inhibited/prevented. In the example of an embodiment illustrated in FIG. 3, the locking component 1036 generally need not be rotated by more than half a turn (less than 180° of rotation) to engage (be seated in) the locking feature 1046.

In some embodiments, a biasing element 230 is provided as a spring assist, such as to assist the flexible elongate member 210 in engaging and pushing the locking component 1036 of the movable component 1010 of the implantable device 1000 into engagement with the locking feature 1046. The biasing element 230 can also act as a spring assist to assure that retraction of the tubular flexible elongate member 220 does not cause retraction of the flexible elongate member 210 so that the actuator latch 212 is exposed distally from the latch cover 222 when the deployment device 200 is shifted to the second stage. In other words, the biasing element 230 assists with the relative axial movement of the actuator latch 212 and the latch cover 222. For instance, the biasing element 230 may be considered to assist in axially pushing the actuator latch 212 out of the latch cover 222 from a distal end of the deployment device 200 rather than pushing only from a proximal end and transmitting such force along the length of the flexible elongate member 210 and/or the tubular flexible elongate member 220. In the example of an embodiment illustrated in FIGS. 2A, 2B, 3, and 4, a distal end 231 of the biasing element 230 is held against movement with respect to the flexible elongate member 210, and a proximal end 233 of the biasing element 230 is held against movement with respect to the latch cover 222. For instance, a distal end 231 of the biasing element 230 may be fixed (e.g., welded or interference fitted) to the flexible elongate member 210 (proximal to the actuator latch 212). Additionally or alternatively, the proximal end 233 of the biasing element 230 may be seated against a seat 225 (e.g., inwardly directed shoulder or narrowing throat) within the latch cover 222. When the deployment device 200 is in stage one, the biasing element 230 stores potential energy (e.g., is in compression) which is released when the deployment device 200 is shifted to stage two, so that the biasing element 230 biases the tubular flexible elongate member 220 and the flexible elongate member 210 apart when the deployment device 200 is shifted from the first stage to the second stage.

Figure 4:
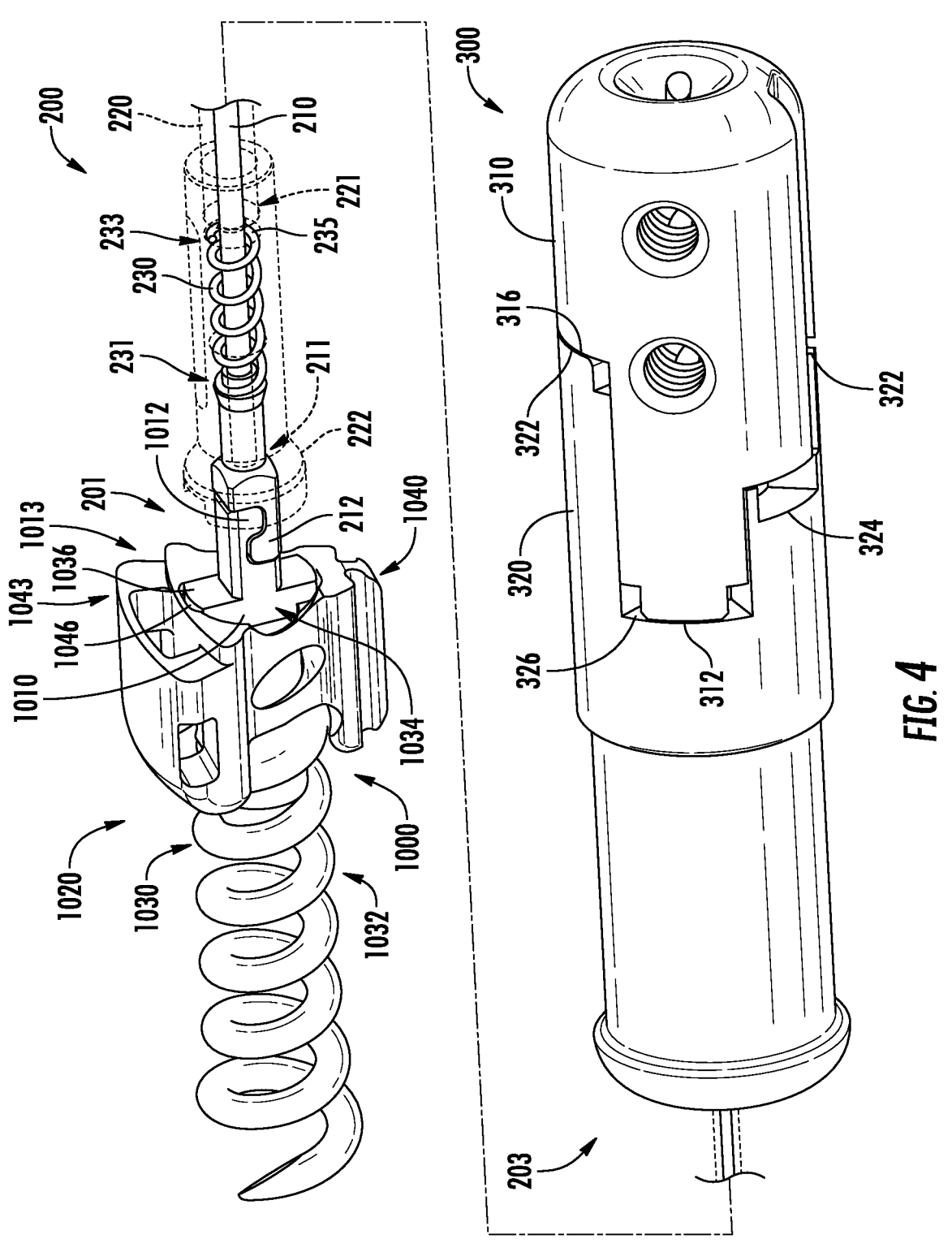
FIG. 4 illustrates a view similar to that of FIG. 2A and FIG. 3, but with the anchor cover further withdrawn to allow disengagement of the anchor actuator from the anchor.

Once the locking component 1036 has been operably engaged with the locking feature 1046, the deployment device 200 may be shifted into the third stage, illustrated in FIG. 4. More particularly, in the third stage, the tubular flexible elongate member 210 is further proximally retracted to proximally retract the latch cover 222 to unsheathe the actuator latch 212 and the component latch 1012 to allow separation thereof, and, thereby, to allow withdrawal of the deployment device 200 from the implantable device 1000.

The components of the deployment device 200 may be actuated in any manner known to those of ordinary skill in the art. For instance, in the example of an embodiment illustrated in FIG. 1, the deployment device 200 is actuated via a control device 300. In accordance with various principles of the present disclosure, the control device 300 includes a control knob at a proximal end of at least one of the flexible elongate member 210 or the tubular flexible elongate member 220. In the example of an embodiment illustrated in further detail in FIGS. 2A, 2B, 3, and 4, the control device 300 includes a latch control knob 310 operably engaged with the flexible elongate member 210 to actuate the flexible elongate member 210, such as to move the actuator latch 212 on the distal end 211 of the flexible elongate member 210, and an actuator control knob 320 operably engaged with the tubular flexible elongate member 220 to actuate the tubular flexible elongate member 220, such as to actuate the deployment device 200 (e.g., to rotate the actuator latch 212 and the component latch 1012 and the movable component 1010).

In accordance with various principles of the present disclosure, a control device 300 which may be used in the example of an embodiment illustrated in FIGS. 1, 2A, 2B, 3, and 4 is shiftable between a first stage, a second stage, and a third stage to correspond with the first stage, second stage, and third stage, respectively, of the deployment device 200. Further in accordance with various principles of the present disclosure, control knobs 310, 320 of the illustrated example of an embodiment of a control device 300 are movable with respect to each other as the control device 300 is shifted between the first, second, and third stages thereof, such as may be appreciated with reference to FIGS. 2A, 2B, 3, and 4. More particularly, the control knobs 310, 320 operably associated with the flexible elongate member 210 and the tubular flexible elongate member 220, respectively, are movable with respect to each other to cause corresponding movements of the flexible elongate member 210 and the tubular flexible elongate member 220, and, more particularly, the actuator latch 212 and the latch cover 222 associated therewith, as will now be described with reference to FIGS. 2A, 2B, 3, and 4.

As illustrated in FIG. 2B, the tubular flexible elongate member 220 is operably coupled with the actuator control knob 320. In some embodiments, the tubular flexible elongate member 220 may be locked with respect to actuator control knob 320 (such as with a set screw 325) so that movement of the actuator control knob 320 is transmitted to the tubular flexible elongate member 220. The flexible elongate member 210 extends proximally through the proximal end 223 of the tubular flexible elongate member 210 so that the proximal end 213 of the flexible elongate member 210 can be operably coupled with the latch control knob 310. The latch control knob 310 may be locked with respect to the flexible elongate member 210 (such as with a set screw 315) so that movement of the latch control knob 310 is transmitted to the flexible elongate member 210.

In the first stage of the deployment device 200, such as illustrated in FIG. 2A, the control device 300 is in a corresponding first stage with the control knobs 310, 320 in a first position with respect to each other. More particularly, in the first stage of the control device 300, the actuator control knob 320 is spaced apart from the latch control knob 310. In such configuration, the deployment device 200 is in the first stage as well, with the latch cover 222 over the actuator latch 212, the component latch 1012, and the locking component 1036 of the movable component 1010 of the implantable device 1000, as described above.

In the second stage of the deployment device 200, such as illustrated in FIG. 3, the control device 300 is in a corresponding second stage with the control knobs 310, 320 in a second position with respect to each other closer together than when the control device 300 is in the first stage. More particularly, in the second stage of the control device 300, the actuator control knob 320 is moved proximally from its position when the control device 300 is in the first stage, and toward the latch control knob 310. Such movement of the actuator control knob 320 proximally retracts the latch cover 222 to unsheathe the movable component 1010 of the implantable device 1000, as described above, shifting the deployment device 200 into the second stage.

In the third stage of the deployment device 200, such as illustrated in FIG. 4, the control device 300 is in a corresponding third stage with the control knobs 310, 320 in a third position with respect to each other closer together than when the control device 300 is in the first stage or the second stage. More particularly, in the third stage of the control device 300, the actuator control knob 320 is moved further proximally from its position when the control device 300 is in the second stage, and toward the latch control knob 310. Such movement of the actuator control knob 320 proximally retracts the latch cover 222 to unsheathe the actuator latch 212 and the component latch 1012, as described above, shifting the deployment device 200 into the third stage and allowing the deployment device 200 to be disengaged and withdrawn from the implantable device 1000.

In accordance with various principles of the present disclosure, the control knobs of the control device 300 may be configured to engage each other or to be operably engaged with each other to maintain a desired position with respect to each other appropriate for each of the three stages of the control device 300. For instance, there may be tension in the flexible elongate members 210 (such as imparted during manufacture or assembly of the deployment system 100) that prevents the control knobs of the control device 300 from moving axially. In some embodiments, the control knobs are configured with various engagement features configured to maintain the control knobs at desired positions with respect to each other corresponding to the stages of the control device 300. In some embodiments, a separate element is provided between the control knobs and is movable to adjust the relative positions of the control knobs. A larger amount of force than the tension within the flexible elongate members 210 may be imparted to move the control knobs with respect to one another.

In the example of an embodiment illustrated in FIGS. 2A, 2B, 3, and 4, the control knobs 310, 320 are shaped and configured to engage each other in at least three different positions/configurations corresponding to a respective different one of the stages of the control device 300 (which, in turn, correspond to one of the respective stages of the deployment device 200). In the illustrated embodiment, the latch control knob 310 has stepped formations 312, 314, 316 configured to engage with corresponding stepped formations 322, 324, 326 on the actuator control knob 320. The formations may include one or more projections or steps on one control knob configured to engage with a corresponding projection or step on the other control knob, such as to hold or maintain the control knobs 310, 320 in the selected configuration and/or to prevent inadvertent/unintended shifting of the control knobs 310, 320 into a different configuration. It will be appreciated that other shapes and configurations of engagement elements of the control knobs 310, 320 are within the scope of the present disclosure, the present disclosure not being limited by details of the illustrated example.

In the example of an embodiment illustrated in FIG. 2A, one of the stepped formation 312 on the latch control knob 310 or the stepped formation 322 on the actuator control knob 320 may be considered a projection fitting in a seat between a pair of projections on the other of the stepped formation 312 on the latch control knob 310 or the stepped formation 322 of the actuator control knob 320. As such, relative rotation between the control knobs 310, 320 is inhibited so that the control knobs 310, 320 do not inadvertently shift to another configuration.

The control knobs 310, 320 may be moved slightly apart from each other to disengage the respective first stepped formations 312, 314 to rotate the control knobs 310, 320 relative to each other to shift the control knobs 310, 320 into another configuration such as the second configuration. In the second configuration, such as illustrated in FIG. 3, the control knobs 310, 320 are moved closer together (e.g., the actuator control knob 320 is moved proximally toward the latch control knob 310) so that the first stepped formation 312 of the latch control knob 310 engages with the second stepped formation 324 of the actuator control knob 320, and the first stepped formation 322 of the actuator control knob 320 engages with the second stepped formation 314 of the latch control knob 310. The second stepped formation 314, 324 of the latch control knob 310 and/or the actuator control knob 320 may be formed with projections on either side of a seat in which the first stepped formation 322 of the actuator control knob 320 and/or the first stepped formation 312 of the latch control knob 310, if configured as a projection, may be seated. Such configuration inhibits relative rotation of the control knobs 310, 320 to inhibit the control knobs 310, 320 from inadvertently shifting into a different configuration. The control knobs 310, 320 may be moved slightly apart from each other to disengage the first stepped formation 312 of the latch control knob 310 from the second stepped formation 324 of the actuator control knob 320 to rotate the control knobs 310, 320 relative to each other to shift the control knobs 310, 320 into another configuration such as the first or the third configuration.

In the third configuration, such as illustrated in FIG. 4, the control knobs 310, 320 are moved even closer together so that the first stepped formation 312 of the latch control knob 310 engages with the third stepped formation 326 of the actuator control knob 320, and the first stepped formation 322 of the actuator control knob 320 engages with the third stepped formation 316 of the latch control knob 310. The third stepped formation 324 of the actuator control knob 320 may be recessed with walls on either side thereof so that the first stepped formation 312 of the latch control knob 310 may be seated therein. Similarly, the third stepped formation 314 of the latch control knob 310 may be recessed with walls on either side thereof so that the first stepped formation 322 of the actuator control knob 320 may be seated therein. Such configuration inhibits relative rotation of the control knobs 310, 320 to inhibit the control knobs 310, 320 from inadvertently shifting into a different configuration.

Figure 5:
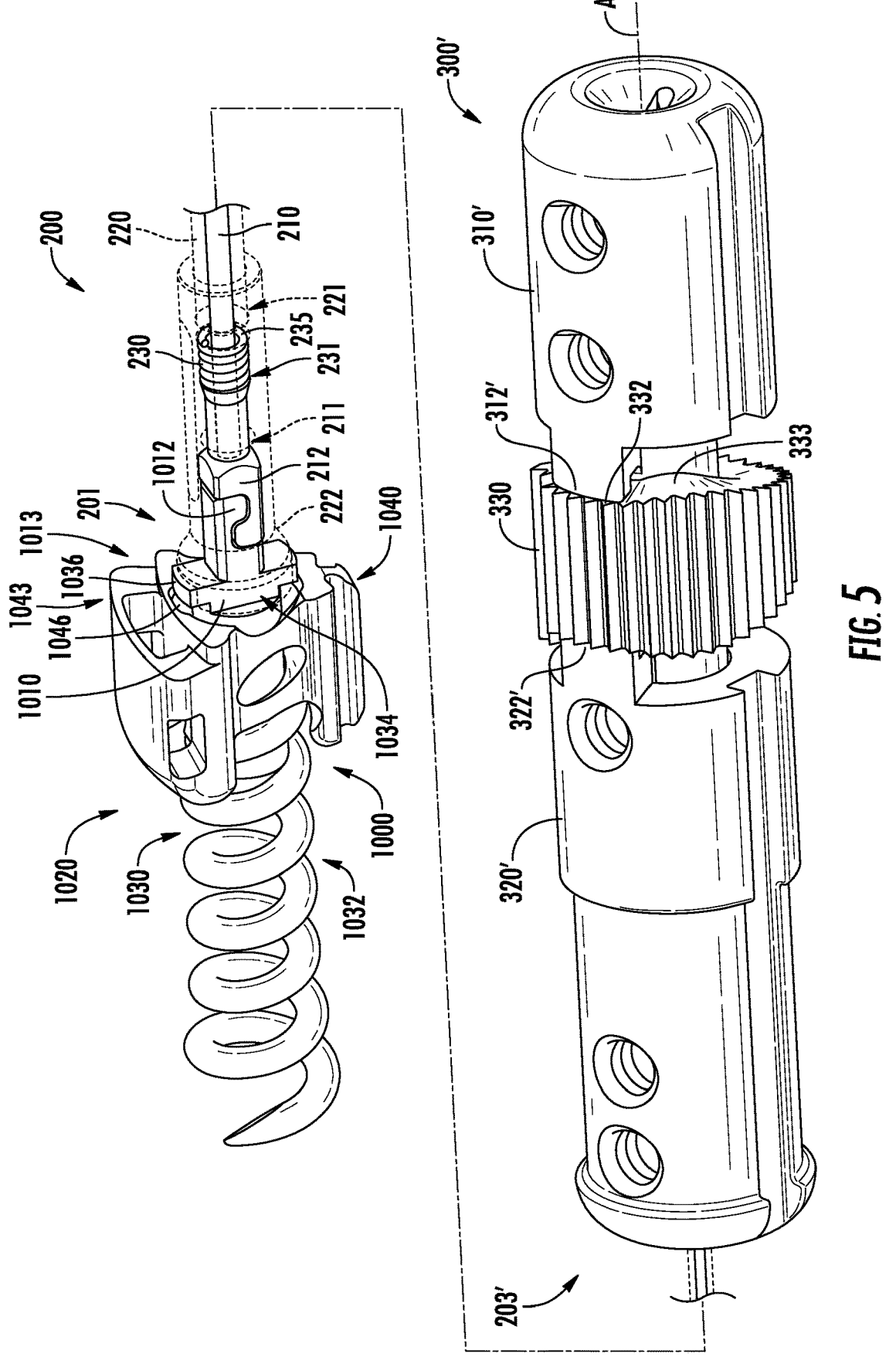
FIG. 5 illustrates a view similar to that of FIG. 2A, but with another embodiment of control knobs.
Figure 6:
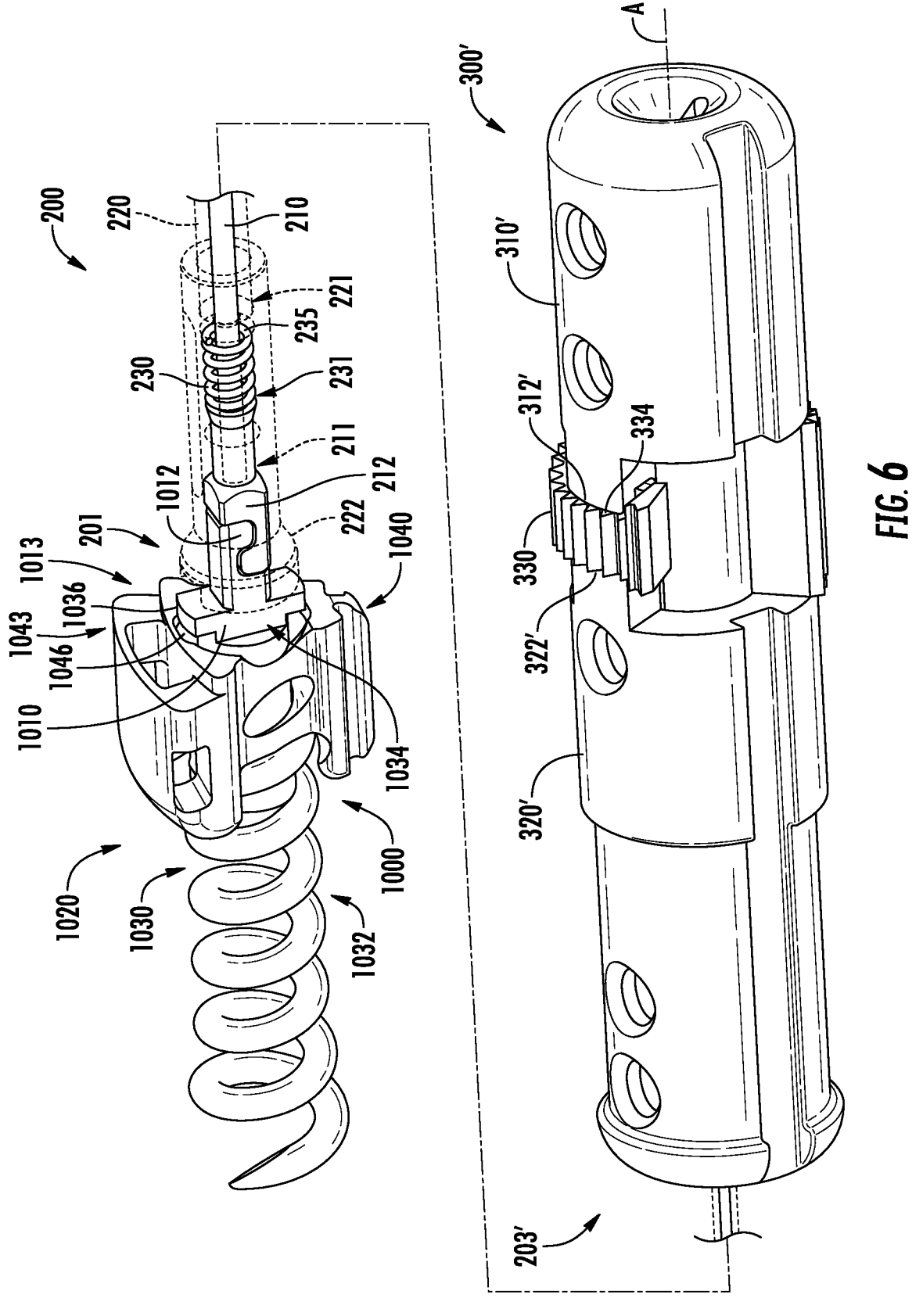
FIG. 6 illustrates a view similar to that of FIG. 5, but with the anchor cover withdrawn to expose a portion of the anchor head.
Figure 7:
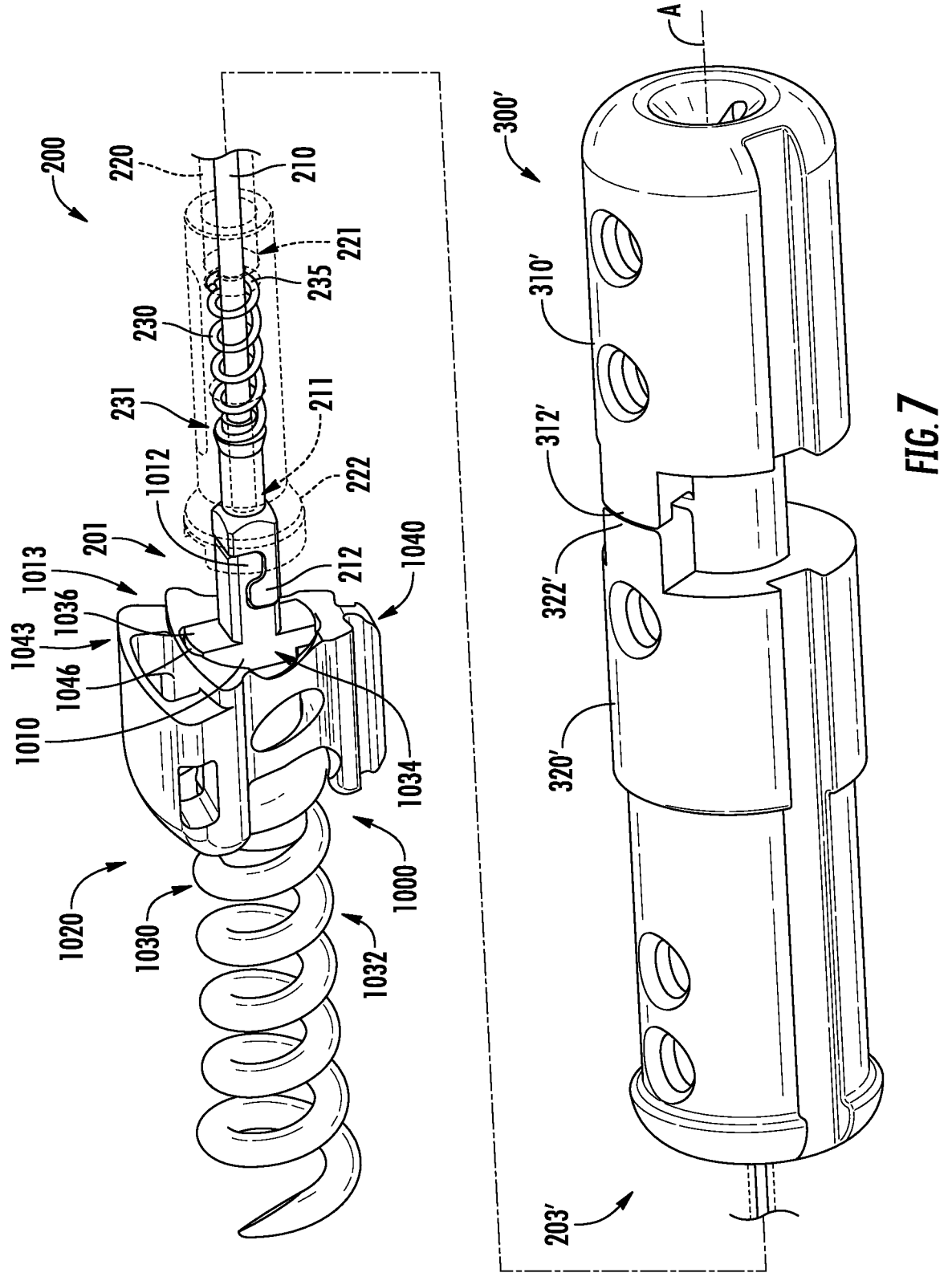
FIG. 7 illustrates a view similar to that of FIG. 5 and FIG. 6, but with the anchor cover further withdrawn to allow disengagement of the anchor actuator from the anchor.

In another embodiment, such as illustrated in FIG. 5, FIG. 6, and FIG. 7, a separate element 330, referenced herein as a clip 330 for the sake of convenience and without intent to limit, is positioned between control knobs 310', 320' of a control device 300'. The control knobs 310', 320' in the example of an embodiment illustrated in FIGS. 5-7 may be substantially similar in form and construction as the control knobs 310, 320 in the example of an embodiment illustrated in FIGS. 2A, 2B, 3, and 4, other than the engaging structures. Instead of rotating the control knobs 310', 320' with respect to each other to adjust the configuration of the control knobs 310', 320' to shift the control device 300 between the various first, second, and third stages thereof, the clip 330 may be rotated with respect to the control knobs 310', 320'. The width of the clip 330 (e.g., a longitudinal extent along an axial direction A of the control knobs 310, 320 and the control device 300) varies along the circumference (about the axial direction A). The clip 330 is positioned between the control knobs 310', 320' and rotated relative to the control knobs 310', 320' to adjust the relative position of the control knobs 310', 320' by adjusting the portion of the clip 330 contacted by the adjacent surfaces of the control knobs 310', 320'.

In the illustrated example of an embodiment, the control knobs 310', 320' each include a respective axial projection 312', 322' engageable with the clip 330. For instance, as illustrated in FIG. 5, in a first configuration of the control knobs 310', 320', the respective axial projections 312', 322' thereof are engageable within a corresponding first recess 332 in the clip 330 at the widest region of the clip 330. The control knobs 310', 320' are thus held apart from each other to correspond to the first stage of the control device 300' and corresponding first stage of the deployment device 200 in which the latch cover 222 extends over the locking component 1036 of the movable component 1010 of the implantable device 1000 as well as over the actuator latch 212 and the component latch 1012. The first recess 322 of the clip 330 may be configured to prevent inadvertent rotation of the clip 330 relative to the control knobs 310, 320. However, a ramped surface 333 may be provided on a side of the first recess 332 from which the clip 330 tapers to a reduced width to allow an intended rotational force to be exerted to allow intentional shifting of the clip 330 into another position relative to the control knobs 310', 320'.

The clip 330 may be rotated from the position illustrated in FIG. 5 to the position illustrated in FIG. 6 by rotating the ramped surface 333 thereof over the projections 312', 322' of the control knobs 310', 320'. In the second configuration of the control knobs 310', 320', as illustrated in FIG. 6, a second recess 334 of the clip 330 is positioned adjacent to the projections 312', 322' of the control knobs 310', 320' for the projections 312', 322' to be seated therein. In such configuration of the control knobs 310', 320', the control device 300' is in its second stage corresponding to a second stage of the deployment device 200 with the latch cover 222 withdrawn from covering the locking component 1036 of the movable component 1010 of the implantable device 1000, yet still covering the actuator latch 212 and the component latch 1012.

The clip 330 may be removed from between the control knobs 310', 320', as illustrated in FIG. 7, to allow the control knobs 310', 320' to shift into a third configuration corresponding to a third stage of the control device 300' and the third stage of the deployment device 200 described above.

It will be appreciated that other forms of engagement structures configured to hold/maintain the control knobs 310', 320' in a desired configuration relative to the clip 330 are within the scope of the present disclosure.

Although embodiments of the present disclosure may be described with specific reference to an implant, such as for use with mitral valves, it is appreciated that various other devices may similarly benefit from the structures and manufacturing methods disclosed herein. For example, devices such as implants which must withstand the palpatory forces for repairing a tricuspid valve annulus and/or addressing other dilatation, valve incompetency, valve leakage and other similar heart failure conditions may also benefit from the concepts disclosed herein. Principles of the present disclosure may be applied to other devices with movable components and not limited to specifically implantable devices.

In view of the above, it should be understood that the various embodiments illustrated in the figures have several separate and independent features, which each, at least alone, has unique benefits which are desirable for, yet not critical to, the presently disclosed mechanisms. Therefore, the various separate features described herein need not all be present in order to achieve at least some of the desired characteristics and/or benefits described herein. Only one of the various features may be present in accordance with various principles of the present disclosure. Alternatively, one or more of the features described with reference to one embodiment can be combined with one or more of the features of any of the other embodiments provided herein. That is, any of the features described herein can be mixed and matched to create hybrid designs, and such hybrid designs are within the scope of the present disclosure. Moreover, throughout the present disclosure, reference numbers are used to indicate a generic element or feature of the disclosed embodiment. The same reference number may be used to indicate elements or features that are not identical in form, shape, structure, etc., yet which provide similar functions or benefits. Additional reference characters (such as letters, as opposed to numbers) may be used to differentiate similar elements or features from one another.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A deployment system for deploying an implantable device at a treatment site, the implantable device having a movable component shiftable between a position in which the movable component is movable with respect to another component of the implantable device and a locked position in which a locking component associated with the movable component locks the movable component with respect to the other component of the implantable device, said deployment system comprising:

a deployment device engageable with the movable component to move the movable component;

wherein the deployment device comprises:

a tubular flexible elongate member having a distal end configured to operably engage a portion of the movable component to impart movement thereto, and a flexible elongate member extending through the flexible elongate member and having, on a distal end thereof, an actuator engagement component configured to engage a corresponding implantable device engagement component on the movable component;

wherein the deployment device is shiftable between:

a first stage in which the deployment device is fully engaged with the movable component and the locking component thereof, a second stage in which the deployment device is operatively engaged with a portion of the movable component to move the movable component and exposes at least a portion of the locking component to allow the locking component to be moved into engagement with respect to the implantable device, and a third stage in which the deployment device is disengaged from the movable component to be withdrawn from the treatment site; and a spring assist between the distal end of the tubular flexible elongate member and the distal end of the flexible elongate member to assist in movement of the distal end of the tubular flexible elongate member and the distal end of the flexible elongate member apart from each other.

2. The deployment system of claim 1, wherein the tubular flexible elongate member is configured to operably engage the actuator engagement component to impart movement thereto.

3. The deployment system of claim 1, further comprising a control device operably coupled with the deployment device and shiftable between a first stage, a second stage, and a third stage corresponding to the first stage, second stage, and third stage of the deployment device.

4. The deployment system of claim 3, wherein the control device comprises an actuator control knob operably coupled with the tubular flexible elongate member, and a latch control knob operably coupled with the flexible elongate member.

5. The deployment system of claim 4, wherein the actuator control knob and the latch control knob are shiftable with respect to each other between first, second, and third configurations corresponding, respectively, to the first stage, the second stage, and the third stage of the control device.

6. The deployment system of claim 5, wherein:

in the first configuration, the actuator control knob and the latch control knob are a first distance apart;

in the second configuration, the actuator control knob and the latch control knob are a second distance apart, the second distance being smaller than the first distance; and in the third configuration, the actuator control knob and the latch control knob are a third distance apart, the third distance being smaller than the second distance.

7. The deployment system of claim 5, wherein the actuator control knob and the latch control knob are shaped and configured to engage each other in one of three different positions each corresponding to one of the first, second, and third configurations.

8. The deployment system of claim 5, wherein the control device further comprises a movable clip positioned between the actuator control knob and the latch control knob and movable between one of three different positions to move the actuator control knob and the latch control knob to a respective corresponding one of the first, second, and third configurations.

9. The deployment system of claim 8, wherein the movable clip has a varying longitudinal extent between the actuator control knob and the latch control knob and is rotatable to vary the distance between the actuator control knob and the latch control knob.

10. An implantable device and a deployment system therefor, comprising:

an implantable device having a movable component shiftable between a position in which the movable component is movable with respect to an other component of the implantable device and a locked position in which a locking component associated with the movable component locks the movable component with respect to the other component of the implantable device; and a deployment system comprising a deployment device engageable with the movable component to move the movable component;

wherein the deployment device comprises:

a tubular flexible elongate member having a distal end configured to operably engage a portion of the movable component to impart movement thereto, and a flexible elongate member extending through the flexible elongate member and having, on a distal end thereof, an actuator engagement component configured to engage a corresponding implantable device engagement component on the movable component;

wherein:

the deployment device is shiftable between:

a first stage in which the deployment device is fully engaged with the movable component and the locking component, a second stage in which the deployment device is operatively engaged with a portion of the movable component to move the movable component and exposes at least a portion of the locking component to allow the locking component to be moved into engagement with respect to the implantable device, and a third stage in which the deployment device is disengaged from the movable component to be withdrawn from engagement with the implantable device;

wherein:

the distal end of the tubular flexible elongate member is configured to engage the locking component and the implantable device engagement component when the deployment device is in the first stage;

in the second stage of the deployment device the distal end of the tubular flexible elongate member extends over the implantable device engagement component and the actuator engagement component in operable engagement with each other, and exposes at least a portion of the locking component to permit engagement of the locking component with the locking feature; and in the third stage of said deployment device the tubular flexible elongate member is withdrawn from the implantable device engagement component and the actuator engagement component to allow disengagement of the implantable device engagement component and the actuator engagement component from each other; and a spring assist between the distal end of the tubular flexible elongate member and the distal end of the flexible elongate member to assist in distal movement of the distal end of the flexible elongate member with respect to the distal end of the tubular flexible elongate member to rotate and engage the locking component with the locking feature.

11. The implantable device and deployment system of claim 10, wherein:

the movable component of the implantable device comprises an anchor having an anchor head at a proximal end thereof;

the locking component is formed on the anchor head; and the implantable device engagement component is formed on the anchor head proximal to the locking component.

12. The implantable device and deployment system of claim 11, wherein:

the implantable device further comprises an anchor housing;

the other component of the implantable device is the anchor housing; and a locking feature is formed in the anchor housing configured for locking engagement of the locking component on the anchor head therewith.

\* \* \* \* \*